United States Patent [19]

Toyoshima et al.

[11] 4,448,788
[45] May 15, 1984

[54] 11-DEOXOGLYCYRRHETINIC ACID HYDROGEN MALEATE, PROCESS FOR ITS PRODUCTION, AND ITS USE AS A MEDICINE

[75] Inventors: Shigeshi Toyoshima, Tokyo; Hajime Fujimura, Kyoto; Shunsuke Ito; Yasuji Kondo, both of Hiroshima, all of Japan

[73] Assignee: Maruzen Pharmaceutical Co., Ltd., Hiroshima, Japan

[21] Appl. No.: 394,114

[22] Filed: Jul. 1, 1982

[30] Foreign Application Priority Data

Jul. 6, 1981 [JP] Japan .................................. 56-104406

[51] Int. Cl.³ ..................... A61K 31/225; C07C 69/60
[52] U.S. Cl. .................................... 424/313; 560/194; 560/204
[58] Field of Search ................. 560/194, 204; 424/313

[56] References Cited

U.S. PATENT DOCUMENTS

| | | | |
|---|---|---|---|
| 3,984,461 | 10/1976 | Pifferi | 560/194 |
| 4,000,186 | 12/1976 | Vanstone | 560/194 |
| 4,061,773 | 12/1977 | Chan | 560/194 X |

*Primary Examiner*—Glennon H. Hollrah
*Assistant Examiner*—Vera C. Clarke
*Attorney, Agent, or Firm*—Sherman & Shalloway

[57] ABSTRACT

11-Deoxoglycyrrhetinic acid hydrogen maleate of the following formula

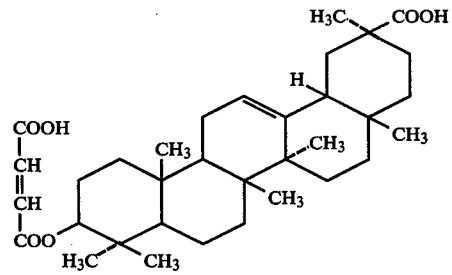

and its salts, and this compound is prepared by reacting 11-deoxoglycyrrhetinic acid with maleic anhydride, and if desired, converting the resulting 11-deoxoglycyrrhetinic acid hydrogen maleate to its salt. The compound is useful as medicament for treating an ulcer or inflammation in man or another animal or activating the cellular immunity of man or the animal.

14 Claims, No Drawings

11-DEOXOGLYCYRRHETINIC ACID HYDROGEN MALEATE, PROCESS FOR ITS PRODUCTION, AND ITS USE AS A MEDICINE

This invention relates to a novel 11-deoxoglycyrrhetinic acid derivative, and more specifically, to 11-deoxoglycyrrhetinic acid hydrogen maleate of the following formula

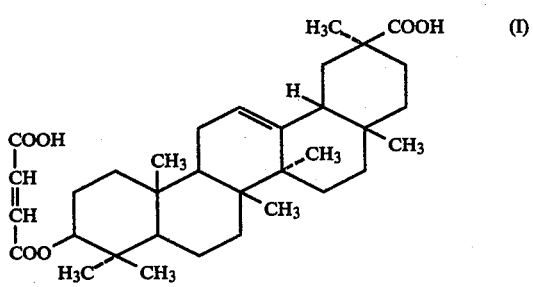

a process for its production, and its use as a medicine, especially as an antiulcer agent, an anti-inflammatory agent, or a cellular immunity activator.

It has been known from old that an extract of licorice (*Glycyrrhiza glabra*) is effective for the treatment of diseases of the digestive organs. Since Revers of Holland announced in 1946 that the licorice extract exhibits an excellent efficacy in the treatment of peptic ulcer [F. E. Revers: Nederl. Tschr. Geneesk., No. 90,135 (1946)], much work was done as to an anti-ulcer active component in the licorice extract, and led to the determination that the main pharmacologically active component of the licorice extract is glycyrrhizin which is a glycoside. Later, many papers were published about the medical and biological properties of glycyrrhizin, its aglycone 18β-glycyrrhetic acid, and its derivatives. A typical example is glycyrrhetinic acid hydrogen succinate sodium salt, also known as carbenoxolone sodium, which is a highly water-soluble glycyrrhetinic acid derivative (see British Pat. No. 843,133) and is actually used as an agent for treating gastric ulcer.

It is known on the other hand that glycyrrhetinic acid and its derivatives have an aldosterone (DCA)-like activity and promote sodium retention and potassium excretion, which are likely to induce serious side-effects such as edema, a decrease in serum potassium level, a rise in blood pressure and myopathy.

J. S. Baran et al. synthesized many derivatives of glycyrrhetinic acid, and screened their anti-DCA, anti-inflammatory, antiviral and antiulcer activities (John S. Baran et al., Journal of Medicinal Chemistry, 1974, Vol. 17, No. 2, pages 184–191). This paper states that 11-deoxoglycyrrhetinic acid does not substantially show the DCA activity of the parent compound.

With the foregoing background, the present inventors synthesized many derivatives of 11-deoxoglycyrrhetinic acid, and examined their biological and pharmacological activities. Consequently, they have found that the compound of formula (I) given above, i.e. a semi-ester formed between 11-deoxoglycyrrhetinic acid and maleic acid, has very good anti-ulcer, anti-inflammatory and delayed-type cellular immunity activating actions without any of the side-effects mentioned above, and therefore, is very suitable as a safe medicine.

As formula (I) shows, 11-deoxoglycyrrhetinic acid hydrogen maleate provided by this invention has two carboxyl groups, and can exist in the form of a salt. Examples of the salt include alkali metal salts such as sodium and potassium salts, alkaline earth metal salts such as magnesium and calcium salts, and an aluminum salt. Among them, pharmaceutically acceptable salts, such as the sodium, potassium and aluminum salts, are preferred.

The compound of formula (I) provided by this invention can be produced by reacting 11-deoxoglycyrrhetinic acid of the following formula

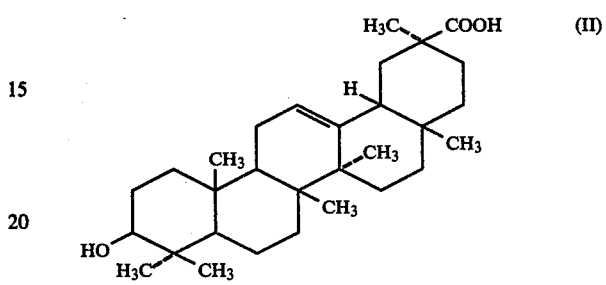

with an ester-forming reactive derivative of maleic acid, such as maleic anhydride.

The above esterification reaction can usually be carried out in an inert organic solvent such as an ether (e.g., dioxane, tetrahydrofuran, etc.), or an aromatic hydrocarbon (e.g., benzene, toluene, xylene, etc.). The reaction temperature is not critical, and can be varied depending upon the type of the ester-forming reactive derivative of maleic acid. When maleic anhydride is used, the reaction temperature is generally about 100° C. to the refluxing temperature of the reaction mixture, preferably the refluxing temperature of the reaction mixture or temperatures near it. The reaction time, which may vary depending upon the reaction temperature used, is generally about 5 to about 40 hours.

The amount of maleic anhydride to be used relative to the compound of formula (II) is neither critical. Usually, the suitable amount of maleic anhydride is 1.5 to 2.0 moles, preferably 2.0 to 3.0 moles, per mole of the compound of formula (II).

The compound of formula (I) can be separated from the reaction mixture, and purified, by methods known per se, such as recrystallization and chromatography.

The compound of formula (I) so obtained may be converted to its salt by treating it with sodium hydroxide, potassium hydroxide, aluminum chloride, etc. in accordance with methods known per se.

The 11-deoxoglycyrrhetinic acid of formula (II) used as a starting material in the above process is a known compound, and can be produced, for example, by dissolving glycyrrhetinic acid in a suitable solvent such as acetic acid, methanol, ethanol, dioxane, or tetrahydrofuran, and reducing it. The reduction may be carried out by a conventional catalytic reducing method using hydrogen in the presence of a catalyst, for example a metal such as platinum or palladium or its oxide.

The compound of formula (I) and its salts provided by this invention are characterized by having excellent antiulcer, antiinflammatory and delayed-type cellular immunity activating actions and extremely low toxicity (particularly in oral administration) and being free from side-effects (e.g., edema, a decrease in serum potassium level, a rise in blood pressure, a myopathy, etc.). Furthermore, the compound of formula (I) and its salts have antitumor activity. Animal experiments shown below can demonstrate the superior biological activities and the low toxicity of the compounds of this invention.

I. Antiulcer activity

In the following test examples, male SD-strain rats (body weight 200 to 250 g) were used as experimental animals, and a sodium salt of the compound of formula (I) dissolved in distilled water was used as the compound of this invention.

TEST EXAMPLE 1

Pylorus ligating method (Shay's ulcer):

Rats, 10 per group, were used, and allowed to fast for 48 hours in separate cages while giving them only water. Pentobarbital sodium was injected intraperitoneally to the rats in a dose of 5 mg per rat. Under anesthesia, the abdomen of each rat was incised, and the portion leading from the pylorus to the duodenum was ligated. Then, the abdomen was sutered. The rats were then left for 19 hours without giving them food and water. Then, under ether anesthesia, the rats were killed by removing the spinal cord. The stomach was excised, and the amount of the gastric juice was measured. The stomach was then cut open along its greater curvature, and placed on a cork plate. The area of an ulcer generated at the anterior stomach was measured by means of an Olympus stereoscope (magnification 10×), and the ulcer index was calculated on the basis of the following criteria.

| Area of the ulcer ($mm^2$) | Ulcer index |
| --- | --- |
| 1–10 | 1 |
| 11–20 | 2 |
| 21–30 | 3 |
| 31–40 | 4 |
| 41 or more, or perforated | 5 |

The test compound of the invention was injected immediately after the ligation, or orally administered 30 minutes before the ligation. To a control group, physiological saline was given at a rate of 1 ml per 100 g of body weight.

The results are shown in Table 1. It is seen that the compound of this invention tested is effective against ulcer induced by ligation of the pylorus, and that the positively effective dose of the compound was about 10 mg/kg in intraperitoneal administration and about 300 mg/kg in oral administration.

TABLE 1

| Dose (mg/kg) | Ulcer index (mean ± standard deviation) | Percent inhibition (%) |
| --- | --- | --- |
| Intraperitoneal | | |
| Control | 4.1 ± 0.51 | — |
| 5 | 3.4 ± 0.84 | 17.1 |
| 10 | 1.4 ± 0.51(**) | 65.9 |
| 20 | 1.2 ± 0.20(**) | 70.7 |
| 50 | 0.3 ± 0.21(***) | 92.7 |
| Intravenous | | |
| Control | 4.2 ± 0.81 | — |
| 40 | 0.4 ± 0.19(***) | 90.4 |
| Subcutaneous | | |
| Control | 5.2 ± 0.50 | — |
| 70 | 0.8 ± 0.90(***) | 84.6 |
| Oral | | |
| Control | 5.0 ± 0.00 | — |
| 100 | 3.2 ± 0.97 | 36.0 |

TABLE 1-continued

| Dose (mg/kg) | Ulcer index (mean ± standard deviation) | Percent inhibition (%) |
| --- | --- | --- |
| 300 | 1.0 ± 1.01(**) | 80.0 |
| 500 | 0.8 ± 0.49(***) | 84.0 |

Note:
The asterisks show the following reliability limits. (This also applies to Tables 2 to 5.)
(**)$P < 0.01$,
(***)$P < 0.001$

TEST EXAMPLE 2

Acetic acid-induced ulcer:

Rats, 5 or 10 per group, were used. After they were anesthetized with pentobarbital sodium, the abdomen was incised, and 0.05 ml of 10% acetic acid was injected into the mucous membrane from the serous layer at the boundary portion in the anterior wall between the body of the stomach and the pylorus part. The abdomen was then sutured. Each of the test drugs shown in Table 2 was intraperitoneally or orally administered once a day for 10 consecutive days beginning with the second day after the above operation. On the 15th day after the operation, the stomach was excised and 12 ml of 1% formalin was injected into it. Then, the stomach was dipped in 1% formalin for 10 minutes, and cut open along the greater curvature. The area of an ulcer generated was measured, and the ulcer index was calculated on the basis of the following standard.

| Area of the ulcer ($mm^2$) | Ulcer index |
| --- | --- |
| 0 | 0 |
| 1–8 | 1 |
| 9–24 | 2 |
| 25–63 | 3 |
| 64–120 | 4 |
| 121–168 | 5 |
| >168 | 6 |

The results are shown in Table 2. It is seen that the compound of this invention, cetraxate hydrochloride and the tissue respiration activator showed significant inhibitions at $P < 0.001$, but the percent inhibition by the compound of this invention was highest.

TABLE 2

| Test drug | Dose (mg/kg) | Ulcer index (mean ± standard deviation) | Percent inhibition (%) |
| --- | --- | --- | --- |
| Intraperitoneal | | | |
| Control | | 3.17 ± 0.167 | — |
| Compound of the invention | 2 | 1.40 ± 0.247(***) | 54.8 |
| Cetraxate hydrochloride | 20 | 1.60 ± 0.245 | 49.5 |
| Tissue respiration activator | | 2.00 ± 0.000 | 36.9 |
| Oral | | | |
| Control | | 2.70 ± 0.949 | — |
| Cetraxate hydrochloride | 50 | 1.90 ± 0.568 | 29.6(*) |
| Carbenoxolone sodium | 300 | 2.36 ± 0.614 | 12.6 |
| Compound of the invention | 10 | 1.60 ± 0.699 | 40.7(***) |
| | 30 | 1.40 ± 0.699 | 48.1(***) |
| | 50 | 1.00 ± 0.817 | 63.0(****) |

Note:
(*)$P < 0.05$,
(****)$P < 0.0001$

The tissue respiration activator used was a calf's blood extract preparation administered at a rate of 0.5 ml per 100 g of body weight (this applies to all tissue respiration activators appearing hereinafter).

TEST EXAMPLE 3

Stress ulcer:

Rats, 5 per group, were used. They were put in wire gauze stress cages (made by Natsume Seisakusho) in an upstanding position. The cages were put in a water bath kept constantly at 23° C., and the rats were immersed to a level of the sternal projection. Each of the drugs shown in Table 3 was administered to the rats intraperitoneally or orally 15 minutes before water immersion. Seven hours after the administration, the rats were knocked out to death. The stomach was excised, and the length of a stress ulcer (erosion) was measured. The results are shown in Table 3.

TABLE 3

| Test drug | Dose (mg/kg) | Length of the erosion (mm) (mean ± standard deviation) | Percent inhibition (%) |
|---|---|---|---|
| Intraperitoneal | | | |
| Control | | 64.84 ± 8.53 | — |
| Compound of the invention | 20 | 19.25 ± 0.95 | 70.3 |
| Cetraxate hydrochloride | 200 | 56.08 ± 12.89 | 13.5 |
| Tissue respiration activator | | 74.84 ± 10.80 | 0 |
| Oral | | | |
| Control | | 76.6 ± 5.90 | — |
| Cetraxate hydrochloride | 300 | 48.6 ± 3.90(**) | 36.6 |
| Compound of the invention | 100 | 9.6 ± 4.80(***) | 87.5 |
| | 300 | 0.0 ± 0.00(***) | 100.0 |
| | 500 | 0.0 ± 0.00(***) | 100.0 |

TEST EXAMPLE 4

Indomethacin-induced ulcer:

Rats, 5 per group, were used. They were caused to fast for 24 hours while giving them only water. Then, indomethacin was subcutaneously injected to the rats in a dose of 30 mg/kg. Eight hours later, the rats were killed, and the stomach was excised and treated in the same way as in Test Example 3. The length of the erosion generated was measured. Each of the test drugs shown in Table 4 was administered to the rats intraperitoneally or orally 10 minutes before the administration of iodomethacin. The results are shown in Table 4.

TABLE 4

| Test drug | Dose (mg/kg) | Length (mm) of the erosion (mean ± standard deviation) | Percent inhibition (%) |
|---|---|---|---|
| Intraperitoneal | | | |
| Control | | 69.85 ± 11.08 | — |
| Compound of the invention | 20 | 17.69 ± 8.08 | 74.7 |
| Cetraxate hydrochloride | 200 | 38.94 ± 8.22 | 44.3 |
| Tissue respiration activator | | 48.60 ± 19.04 | 30.4 |
| Oral | | | |
| Control | | 56.13 ± 6.39 | — |
| Cetraxate hydrochloride | 300 | 31.58 ± 7.59 | 43.7(*) |
| Compound of the invention | 100 | 9.37 ± 3.22 | 83.3(***) |
| | 300 | 7.22 ± 3.06 | 87.1(***) |
| | 500 | 5.63 ± 3.92 | 90.0(***) |

II. Anti-inflammatory activity

Female Donryu-strain rats (body weight 170±10 g), 10 per group, were used in an anti-inflammatory activity test.

The sodium salt of the compound of formula (I) was used as the compound of this invention. It was uniformly mixed with macrogol (a mixture of equal amounts of polyethylene glycol 400 and polyethylene glycol 4000) to form ointments having the varying concentrations as shown in Table 5.

0.05 ml of a 1% aqueous carrageenan solution as an inflammation-inducing agent was inoculated subcutaneously in the foot pad of the right hind legs of each of the rats. Immediately after the inoculation, the pad was wrapped with a gauze (3×3 cm) coated with each of the ointments. The volume of the foot was measured before the inoculation of the inflammation-inducing agent and 3 hours after the inoculation. The percent edema and percent inhibition at 3 hours after the inoculation were calculated in accordance with the following equations.

$$\text{Percent edema (\%)} = \frac{(Vt - Vn)}{Vn} \times 100$$

Vn: the volume of the foot before the inoculation of the inflammation-inducing agent, Vt: the volume of the foot 3 hours after the inoculation.

$$\text{Percent inhibition (\%)} = \frac{(Ec - Et)}{Ec} \times 100$$

Ec: the percent edema of a non-treated group,

Et: the percent edema of a group treated with the drug.

The results are shown in Table 5. It is seen that the ointments containing at least 0.1% of the compound of this invention significantly inhibited carrageenan edema.

TABLE 5

| Test drug | Percent edema (%) (mean ± standard deviation) | Percent inhibition (%) |
|---|---|---|
| Non-treated | 13.2 ± 1.78 | — |
| Macrogol alone | 12.6 ± 0.76 | 4.5 |
| 0.1% Ointment | 9.8 ± 0.80(*) | 25.7 |
| 0.2% Ointment | 9.0 ± 0.60(**) | 31.8 |
| 0.3% Ointment | 8.5 ± 0.40(**) | 35.6 |
| 0.5% Ointment | 8.0 ± 0.60(**) | 39.3 |
| 1.0% Ointment | 7.9 ± 0.50(**) | 40.1 |

III. Delayed-type cellular immunity activating action

Mice, 10 per group, were used. Sheep red blood cells ($1.0 \times 10^7$) were subcutaneously inoculated in the right foot pad of each mouse. The day of inoculation was taken as day 0, and on the same day, the sodium salt of the compound of formula (I) was administered to the mice intraperitoneally or orally. On day 7, sheep red blood cells ($1.0 \times 10^7$) were subcutaneously inoculated in the left foot pad of each mouse, and on day 8, the thickness of each foot pad was measured. The results are shown in Table 6.

TABLE 6

| Test drug | Dose (mm/kg) | Thickness of the foot pad (mm) (mean ± standard deviation) | Ratio to the control group |
|---|---|---|---|
| Control | | 25.4 ± 2.6 | 1.00 |
| Compound of the invention | 5 (intraperitoneal) | 30.0 ± 1.8 | 1.18 |
| Compound of the invention | 15 (intraperitoneal) | 37.9 ± 1.2 | 1.49 |
| Compound of the invention | 100 (oral) | 35.6 ± 2.2 | 1.40 |
| Picibanil(*) | 1 KE/mouse (intraperitoneal) | 40.2 ± 1.3 | 1.58 |

Note:
(*): Picibanil is a dried product of Erysipelococcus. 1 KE corresponds to 0.1 mg.

IV. Toxicity

The compound of this invention [the sodium salt of the compound of formula (I)] was administered to rats, and the rats were observed for 7 days. The $LD_{50}$ value was calculated by the method of Reed and Muench. It was found that the $LD_{50}$ of the compound of this invention was more than 6000 mg/kg in oral administration, 67.8 mg/kg in intraperitoneal administration, 54.2 mg/kg in intravenous injection, and 98.3 mg/kg in subcutaneous injection.

Since as demonstrated above, the compound of formula (I) or its salt provided by this invention has excellent antiulcer, anti-inflammatory and delayed-type cellular immunity activating actions and low toxicity, it can be used as an antiulcer agent, an anti-inflammatory agent or a cellular immunity activator for the treatment of peptic ulcer (particularly, gastric ulcer) and inflammation in man and other animals, and/or activating the cellular immunity of these animals.

The 11-deoxoglycyrrhetinic acid hydrogen maleate of formula (I) or its salt provided by this invention can be administered singly to man and other animals as a medicament. Generally, however, it is administered as a pharmaceutical preparation comprising a mixture of such a compound with a pharmaceutically compatible inert organic or inorganic diluent or carrier. Examples of useful inert diluents or carriers include water, gelatin, gum arabic, lactose, starch and its derivatives, cellulose and its derivatives, magnesium stearate, vegetable oils, polyalkylene glycols, Vaseline, talc, aluminum silicate, aluminum magnesium silicate, calcium carbonate, polyvinyl pyrrolidone, lactose, and crystalline cellulose.

The pharmaceutical preparation may be formed into any desired unit dosage form suitable for oral, parenteral or topical application. For example, it may be in the form of a solid preparation such as a powder, granules, tablets (including sugar-coated ones), capsules and a suppository, a liquid preparation such as an injectable, a solution, a suspension or an emulsion, or a semi-solid preparation such as an ointment and cream. As required, these preparations may be sterilized, and/or may contain other pharmaceutical adjuvants such as antiseptics, stabilizers, wetting agents, emulsifiers, salts for changing osmotic pressures, and buffers. They may further include other therapeutically valuable agents. When the compound of formula (I) or its salt is to be used as an injecting preparation, it may be converted to a dried (or lyophilized) powder, and then diluted with a diluent such as water or physiological saline.

The above preparations may contain generally 0.1 to 95% by weight of the compound of formula (I) or its salt although the concentration may vary depending upon their form. For example, the concentration of the compound of formula (I) or its salt may be 0.2 to 0.4% by weight for injectables, 20 to 50% by weight for solid oral preparations, and 0.2 to 1% by weight for topical coating preparations.

The compound of formula (I) or its salt may be administered orally, parenterally or topically. Usually, it is advantageously administered through the oral route. The dosage of the compound of formula (I) or its salt may be varied depending upon the type, age, body weight, etc. of an animal to which it is to be administered. For example, for each human adult per day, it is about 10 to about 20 mg for administration by injection, and about 50 to about 500 mg for oral administration. For topical application, it may suitably be administered as an ointment or cream containing 0.2 to 1.0% of the active ingredient. The daily dose mentioned above may be a single daily dose, or may be divided into several dosages. The aforesaid dose ranges are tentative standards and may be varied below or above the given ranges depending upon the condition, age and body weight of the patient, the physician's judgment, etc.

The following Examples illustrate the present invention further.

EXAMPLE 1

Fifty grams of 11-deoxoglycyrrhetinic acid and 30 g of maleic anhydride were dissolved in 250 ml of anhydrous dioxane. With stirring, the mixture was refluxed at its boiling point for 40 hours. After the reaction, the reaction mixture was left to stand overnight. The precipitated crystals were collected by suction-filtration, washed with about 100 ml of 99% methanol and then with hot water, and dried to give 53 g (yield 87%) of white needlelike crystals having a melting point of 274° to 281° C.

Recrystallization of the product from an azeotropic solvent composed of ethylene chloride and methanol gave crystals having a melting point of 279° to 281° C.

EXAMPLE 2

Anhydrous xylene (250 ml) was added to 50 g of 11-deoxoglycyrrhetinic acid and 30 g of maleic anhydride, and with stirring, the mixture was refluxed at its boiling point for 7 hours. After the reaction, the reaction mixture was left to stand overnight. The precipitated crystals were collected by suction-filtration, washed with about 100 ml of 99% methanol and then with hot water, and dried to give 57 g (yield 94%) of crystals having a melting point of 279° to 281° C.

| Molecular weight: 554.77 ($C_{34}H_{50}O_6$) | | |
|---|---|---|
| Elemental analysis for $C_{34}H_{50}O_6$: | | |
| | C | H |
| Calculated (%) | 73.61 | 9.08 |
| Found (%) | 73.66 | 9.11 |

Field emission-type mass analysis: M/Z 554 M+ (parent peak).

Nuclear magnetic resonance spectrum:

The chemical shift (ppm) of this product was at 6.51 and 6.71, and the coupling constants of these chemical shifts were both 12.0 Hz. The chemical shift of monomethyl maleate was at 6.42 and 6.63, and the coupling constants of these chemical shifts were both 11.5 Hz. On the other hand, the chemical shifts of monomethyl fumarate were 6.95 and 7.38, and their coupling constants were 15 Hz. From the above results, the product obtained was determined to be a semiester of maleic acid.

EXAMPLE 3

Ethanol (100 ml) was added to 50 g of 11-deoxoglycyrrhetinic acid hydrogen maleate, and with stirring, a 10% aqueous solution of sodium hydroxide was added dropwise for neutralization. The mixture was filtered, and the filtrate was concentrated under reduced pressure and dried to give a sodium salt of 11-deoxoglycyrrhetinic acid hydrogen maleate.

A similar treatment using potassium hydroxide gave a potassium salt of the above hydrogen ester.

EXAMPLE 4

Ethanol (100 ml) was added to 50 g of 11-deoxoglycyrrhetinic acid hydrogen maleate, and with stirring, a 10% aqueous solution of sodium hydroxide was added dropwise for neutralization. The mixture was filtered, and to the filtrate was added dropwise a solution of 14.4 g of aluminum chloride ($AlCl_3.6H_2O$) in 20 ml of water with stirring. The precipitated crystals were collected by filtration, washed with water until no chlorine ion was detected. Then, they were dried to give an aluminum salt of 11-deoxoglycyrrhetinic acid hydrogen maleate.

The following examples illustrate the production of pharmaceutical preparations containing the compound of formula (I) or its salt as an active ingredient.

EXAMPLE A

| | |
|---|---|
| Sodium salt of the compound of the invention | 10 parts |
| Synthetic aluminum silicate | 10 parts |
| Lactose | 80 parts |

The above ingredients were uniformly mixed, and reduced to a powder or fine particles in a customary manner.

EXAMPLE B

| | |
|---|---|
| Sodium salt of the compound of the invention | 50 parts |
| Lactose | 20 parts |
| Carboxymethyl cellulose calcium | 10 parts |
| Crystalline cellulose | 20 parts |

The above ingredients were uniformly mixed, compressed, pulverized, and then sieved to form granules.

EXAMPLE C

99 Parts of the granules obtained in Example B were mixed with 1 part of magnesium stearate. The mixture was compression-molded to form tablets each having a diameter of 7 mm.

EXAMPLE D

Fifty milligrams of the sodium salt of the compound of formula (I) was mixed with 50 mg of calcium carbonate. The mixture was reduced to a fine powder and encapsulated to form capsules.

EXAMPLE E

| | |
|---|---|
| Sodium salt of the compound of the invention | 0.2 part |
| HCO-60 (polyoxyethylene-hardened castor oil) | 0.8 part |
| Distilled water | 99 parts |

The above ingredients were mixed and dissolved. The solution was filtered, and then filled in ampoules for injection. The ampoules were sterilized to form an injecting preparation.

If 2 parts of sodium citrate or sodium acetate is used instead of HCO-60, the pH stability of the resulting preparation will be increased.

EXAMPLE F

The sodium salt of the compound of formula (I) of this invention was dissolved in purified water, and mixed well with a hydrophilic ointment of the following recipe described in the Pharmacopoeia of Japan to prepare a hydrophilic ointment containing 0.5 to 2.0% of the compound of the invention.

| Pharmacopoeia of Japan: Hydrophilic ointment (corresponding to USP XIX Hydrophilic Ointment) | |
|---|---|
| White Vaseline | 250 g |
| Stearyl alcohol | 220 g |
| Propylene glycol | 120 g |
| Sodium laurylsulfate | 15 g |
| Ethyl p-hydroxybenzoate or methyl p-hydroxybenzoate | 0.25 g |
| Propyl p-hydroxybenzoate | 0.15 g |
| Purified water | ad. 1000 g |

More specifically, white Vaseline and stearyl alcohol were warmed to dissolve them and maintained at 75° C. The remaining ingredients of the above recipe and 5 to 20 g of the compound of the invention were dissolved in purified water by warming and kept at 75° C. The two solutions were mixed and stirred until the mixture was solidified.

What we claim is:

1. A compound of the following formula

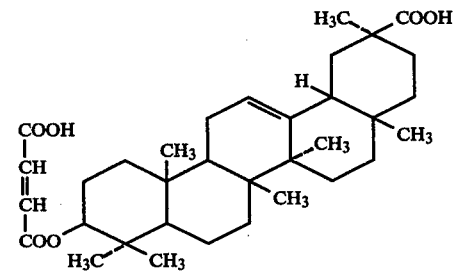

and its salts.

2. A sodium, potassium, or aluminum salt of the compound of claim 1.

3. A pharmaceutical preparation suitable for the treatment of ulcers or as an anti-inflammatory agent or as a cellular immunity activator, comprising as an active ingredient a pharmaceutically effective amount of a compound of the following formula

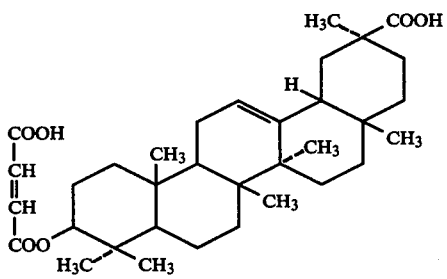

or its pharmaceutically acceptable salt, and a pharmaceutically compatible inert diluent or carrier.

4. The pharmaceutical preparation of claim 3 which is in a unit dosage form.

5. The pharmaceutical preparation of claim 3 which is in the form of a powder, granules, tablets, capsules, an injectable, a suppository, an ointment, or a cream.

6. The pharmaceutical preparation of claim 3 wherein the amount of the active ingredient is 0.1 to 95% by weight.

7. A method for treating an ulcer or inflammation in man or another animal or activating the cellular immunity of man or the animal, which comprises administering a therapeutically effective amount of the compound of claim 1 alone, or a therapeutically effective amount of the pharmaceutical preparation of any one of claims 3 to 6, to man or the animal.

8. The method of claim 7 for treating peptic ulcers in humans which comprises orally administering a therapeutically effective amount of a pharmaceutical preparation comprising as an active ingredient a compound of the following formula

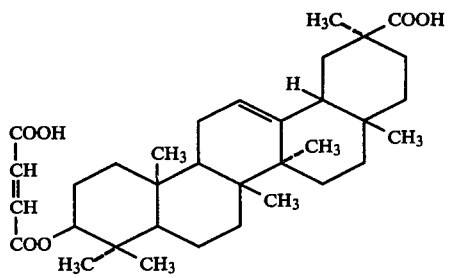

or a pharmaceutically acceptable salt thereof.

9. The method of claim 8 which comprises orally administering from about 50 to about 500 milligrams per day of the active ingredient.

10. The method of claim 7 for treating inflammation which comprises topically administering to the site of inflammation a therapeutically effective amount of a compound of the following formula

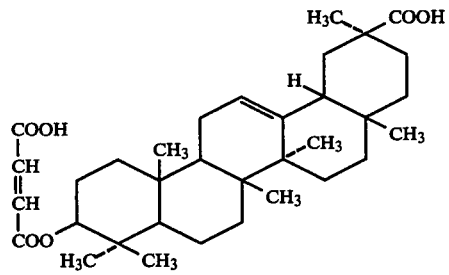

or a pharmaceutically acceptable salt thereof.

11. The method of claim 7 for activating cellular immunity in man.

12. The pharmaceutical preparation of claim 3 in the form of an injectable preparation containing from 0.2 to 0.4% by weight of the active ingredient.

13. The pharmaceutical preparation of claim 3 in the form of a solid oral preparation which comprises from 20 to 50% by weight of the active ingredient.

14. The pharmaceutical preparation of claim 13 in the form of a topical coating preparation which comprises from about 0.2 to 1% by weight of the active ingredient.

* * * * *